(12) United States Patent
Kosa et al.

(10) Patent No.: US 8,932,327 B2
(45) Date of Patent: Jan. 13, 2015

(54) ANCHORING DEVICE

(75) Inventors: Timothy D. Kosa, Hamden, CT (US); Nicholas Maiorino, Branford, CT (US)

(73) Assignee: Covidien LP, Mansfield, MA (US)

( * ) Notice: Subject to any disclaimer, the term of this patent is extended or adjusted under 35 U.S.C. 154(b) by 822 days.

(21) Appl. No.: 12/416,421

(22) Filed: Apr. 1, 2009

(65) Prior Publication Data

US 2009/0248067 A1    Oct. 1, 2009

Related U.S. Application Data

(63) Continuation-in-part of application No. 12/362,002, filed on Jan. 29, 2009.

(60) Provisional application No. 61/041,302, filed on Apr. 1, 2008.

(51) Int. Cl.
*A61B 17/04* (2006.01)
*A61B 17/06* (2006.01)

(52) U.S. Cl.
CPC ....... *A61B 17/06166* (2013.01); *A61B 17/0401* (2013.01); *A61B 2017/0412* (2013.01); *A61B 2017/06176* (2013.01)
USPC .......................................... 606/228

(58) Field of Classification Search
CPC ..................... A61B 17/0401; A61B 17/06166; A61B 2017/06176
USPC ........................... 606/139, 144–150, 222–233
See application file for complete search history.

(56) References Cited

U.S. PATENT DOCUMENTS

| | | | |
|---|---|---|---|
| 3,657,056 A | 4/1972 | Winston et al. | |
| 4,024,871 A | 5/1977 | Stephenson | |
| 5,019,093 A | 5/1991 | Kaplan et al. | |
| 5,059,213 A | 10/1991 | Chesterfield et al. | |
| 5,123,913 A | 6/1992 | Wilk et al. | |
| 5,133,738 A | 7/1992 | Korthoff et al. | |
| 5,181,923 A | 1/1993 | Chesterfield et al. | |
| 5,226,912 A | 7/1993 | Kaplan et al. | |
| 5,236,563 A | 8/1993 | Loh | |
| 5,259,846 A * | 11/1993 | Granger et al. | ............... 606/224 |
| 5,261,886 A | 11/1993 | Chesterfield et al. | |
| 5,306,289 A | 4/1994 | Kaplan et al. | |
| 5,318,575 A | 6/1994 | Chesterfield et al. | |
| 5,342,376 A | 8/1994 | Ruff | |

(Continued)

FOREIGN PATENT DOCUMENTS

| | | |
|---|---|---|
| EP | 0494636 A | 7/1992 |
| EP | 0 499 048 A1 | 8/1992 |

(Continued)

OTHER PUBLICATIONS

European Search Report for Appln. No. 09251035.3 dated Jun. 3, 2009.

(Continued)

*Primary Examiner* — Melanie Tyson

(57) ABSTRACT

An anchoring device having an elongate body at a proximal portion, a distal portion of the elongate body forming a loop at a distal portion of the anchoring device. The loop further includes a plurality of anchors disposed along a surface thereof and the loop also including an end effector. Methods for securing anchoring devices of the present disclosure are also disclosed.

10 Claims, 8 Drawing Sheets

(56) References Cited

U.S. PATENT DOCUMENTS

| | | |
|---|---|---|
| 5,370,031 A | 12/1994 | Koyfman et al. |
| 5,383,387 A | 1/1995 | Chesterfield et al. |
| 5,383,883 A | 1/1995 | Wilk et al. |
| 5,417,700 A | 5/1995 | Egan |
| 5,569,302 A | 10/1996 | Proto et al. |
| 5,662,682 A | 9/1997 | Chesterfield et al. |
| 5,667,528 A | 9/1997 | Colligan |
| 5,814,056 A | 9/1998 | Prosst et al. |
| 5,830,234 A | 11/1998 | Wojciechowicz et al. |
| 5,893,880 A | 4/1999 | Egan et al. |
| 5,931,855 A | 8/1999 | Buncke |
| 5,964,765 A | 10/1999 | Fenton, Jr. et al. |
| 5,968,077 A | 10/1999 | Wojciechowicz et al. |
| 6,063,105 A | 5/2000 | Totakura |
| 6,106,505 A | 8/2000 | Modak et al. |
| 6,143,352 A | 11/2000 | Clark et al. |
| 6,165,202 A | 12/2000 | Kokish et al. |
| 6,174,324 B1 | 1/2001 | Egan et al. |
| 6,203,564 B1 | 3/2001 | Hutton et al. |
| 6,217,591 B1 | 4/2001 | Egan et al. |
| 6,235,869 B1 | 5/2001 | Roby et al. |
| 6,241,747 B1 | 6/2001 | Ruff |
| 6,286,746 B1 | 9/2001 | Egan et al. |
| 6,488,690 B1 | 12/2002 | Morris et al. |
| 6,506,197 B1* | 1/2003 | Rollero et al. ............... 606/148 |
| 6,562,051 B1 | 5/2003 | Bolduc et al. |
| 6,599,310 B2 | 7/2003 | Leung et al. |
| 6,620,846 B1 | 9/2003 | Jonn et al. |
| 6,692,499 B2 | 2/2004 | Tormala et al. |
| 6,773,450 B2 | 8/2004 | Leung et al. |
| 6,923,824 B2 | 8/2005 | Morgan et al. |
| 7,090,111 B2 | 8/2006 | Egan et al. |
| 2002/0077661 A1 | 6/2002 | Saadat |
| 2002/0177876 A1 | 11/2002 | Roby et al. |
| 2003/0074023 A1 | 4/2003 | Kaplan et al. |
| 2003/0097148 A1 | 5/2003 | Valimaa et al. |
| 2003/0149447 A1* | 8/2003 | Morency et al. ............... 606/228 |
| 2004/0010275 A1 | 1/2004 | Jacobs et al. |
| 2004/0030354 A1 | 2/2004 | Leung et al. |
| 2004/0060409 A1 | 4/2004 | Leung et al. |
| 2004/0060410 A1 | 4/2004 | Leung et al. |
| 2004/0087974 A1 | 5/2004 | Bittar |
| 2004/0088003 A1 | 5/2004 | Leung et al. |
| 2004/0122451 A1 | 6/2004 | Wood |
| 2004/0153125 A1 | 8/2004 | Roby |
| 2004/0162580 A1 | 8/2004 | Hain |
| 2005/0033367 A1 | 2/2005 | Leung et al. |
| 2005/0049635 A1 | 3/2005 | Leiboff |
| 2005/0165448 A1 | 7/2005 | Egan et al. |
| 2005/0209639 A1 | 9/2005 | Gidwani et al. |
| 2005/0216058 A1 | 9/2005 | Egan et al. |
| 2005/0267479 A1 | 12/2005 | Morgan et al. |
| 2005/0267531 A1 | 12/2005 | Ruff et al. |
| 2006/0116718 A1 | 6/2006 | Leiboff |
| 2006/0206096 A1 | 9/2006 | Accisano, III et al. |
| 2007/0005110 A1 | 1/2007 | Collier et al. |
| 2007/0021780 A1 | 1/2007 | Harrington et al. |
| 2007/0083236 A1* | 4/2007 | Sikora et al. ............... 606/232 |
| 2007/0187861 A1 | 8/2007 | Genova |
| 2007/0224237 A1 | 9/2007 | Hwang et al. |
| 2008/0281357 A1* | 11/2008 | Sung et al. ............... 606/232 |

FOREIGN PATENT DOCUMENTS

| | | |
|---|---|---|
| EP | 0 632 999 A | 1/1995 |
| EP | 0 632 999 A1 | 1/1995 |
| EP | 0 647 452 A1 | 4/1995 |
| EP | 1 669 093 | 6/2006 |
| EP | 1 656 890 B1 | 12/2008 |
| EP | 2 106 752 A1 | 10/2009 |
| WO | WO 91/07916 A1 | 6/1991 |
| WO | WO 97/08238 | 3/1997 |
| WO | WO 98/00065 | 1/1998 |
| WO | WO 98/52473 | 11/1998 |
| WO | WO 99/52451 A | 10/1999 |
| WO | WO 00/57933 A1 | 10/2000 |
| WO | WO 01/52751 A | 7/2001 |
| WO | WO 03/001979 A2 | 1/2003 |
| WO | WO 2004/014236 A1 | 2/2004 |
| WO | WO 2004/030520 A2 | 4/2004 |
| WO | WO 2004/030704 A2 | 4/2004 |
| WO | WO 2004/030705 A2 | 4/2004 |
| WO | WO 2004/045663 | 6/2004 |
| WO | WO 2004/066927 | 8/2004 |
| WO | WO 2005/080495 | 1/2005 |
| WO | WO 2006/079469 | 8/2006 |
| WO | WO 2007/133103 A | 11/2007 |
| WO | WO 2007/133103 A1 | 11/2007 |
| WO | WO 2008/042909 A | 4/2008 |
| WO | WO 2008/107919 A | 9/2008 |
| WO | WO 2008/141034 A1 | 11/2008 |
| WO | WO 2008/141034 A1 | 11/2008 |

OTHER PUBLICATIONS

European Search Report for Appln. No. 09250460 dated Jun. 2, 2009.
U.S. Appl. No. 60/994,173, filed Sep. 17, 2007, Malorino et al.
JLT1204-211-229(175):R.R. Szarmach et al., Journal of Long-Term Effects of Medical Implants, "An Innovative Surgical Suture and Needle . . . " 12(4), pp. 211-229(2002).
George Odian, "Principles of Polymerization," III Edition, pp. 569-573(1991).
International Search Report from Appln. No. EP 06 012688 dated Aug. 1, 2007.
European Search Report from Appln. No. EP 07 253438 dated Feb. 1, 2008.
European Search Report from application No. 07 25 4341 dated Apr. 20, 2009.
European Search Report for EP 092510346-1265 date of completion is May 26, 2009 (3 pages).
European Search Report from application No. 07 25 4703 dated Feb. 10, 2009.
European Search Report for EP 10177651.6-1526 date of completion is Dec. 14, 2010 (3 pages).
European Search Report for EP 11250537.1269 date of completion is Aug. 8, 2011 (3 pages).
European Search Report for EP 12169125.7-1269 date of completion is Jun. 22, 2012 (5 pages).
European Search Report for EP 12166183.9-1269 date of completion is Jul. 5, 2012 (8 pages).

* cited by examiner ated Jan. 29, 2009, which
ANCHORING DEVICE

CROSS-REFERENCE TO RELATED APPLICATIONS

This application is a continuation in part of U.S. patent application Ser. No. 12/362,002 filed Jan. 29, 2009, which claims the benefit of and priority to U.S. Provisional Patent Application 61/041,302 filed Apr. 1, 2008, the disclosure of which is hereby incorporated by reference herein.

TECHNICAL FIELD

The present disclosure relates generally to the field of surgical devices, and more particularly to anchoring devices, such as sutures, which include a loop having anchors disposed along a surface.

BACKGROUND OF RELATED ART

Surgical sutures have been successfully used for various types of medical procedures, including tissue and wound closure. Surgical sutures typically have a needle attached at one end. As the needle penetrates tissue, the suture enters, passes through, and exits tissue, at which point knots may be used to secure the tissue or wound.

Additionally, sutures typically employ a knot at the distal end to secure the suture end in tissue, permitting movement of the free end through tissue. Knot tying adds time to a procedure and may result in additional bulk material being left at the wound site. Improvements in the field are desired.

Furthermore, specific patient populations such as patients with diabetes T1, T2, or other immuno-compromised patients (such as chemotherapy patients) have less elastic tissue. These patient populations have longer healing profiles and less compliant tissue and these factors may lead to lower suture holding forces in tissue. Needles tend to be oversized for given suture diameter and a larger needle may leave behind a larger hole at the needle penetration point in the tissue. The suture generally needs to fill this hole. Also, improvements in suture holding forces are desired.

SUMMARY

The present disclosure relates to methods for securing, and more specifically methods for securing tissue using anchoring devices. The method includes the steps of providing a suture having a proximal portion and a distal portion wherein the proximal portion includes an elongate body and the distal portion of the suture terminates in a loop, and at least a portion of the loop includes a plurality of barbs and the suture further includes a bifurcation of the elongate body into two branches. The method includes inserting the proximal portion of the suture into a tissue penetration point; advancing the two branches of the suture through the tissue such that the two branches are simultaneously pulled through a penetration point; and securing the suture in the tissue. The method may further include the step of inserting the proximal portion of the suture through a segment of the loop remaining outside the body tissue. The method may further include the step of pulling the suture through tissue until movement of the loop through tissue is limited by an end effector.

Additionally, the passage of the two branches of the loop through the penetration points may lead to an increase the holding force of the suture in tissue. The two branches also exert pressure on the tissue at the penetration point. The two branches of the anchoring device further includes barbs on a surface thereof and these barbs may secure the two branches in the body tissue.

In some embodiments, the anchoring device includes and end effector which limits movement of at least a portion of the loop through tissue such that a segment of the loop remains outside the body tissue. In certain embodiments, the end effector engages the tissue to prevent movement of the loop in a proximal direction.

The present disclosure also contemplates an anchoring device having an elongate body including a proximal portion and a distal portion, the proximal portion of the elongate body terminating in a free end and the distal portion of the elongate body forming a loop; the loop includes a first plurality of anchors disposed along a surface of the loop and the loop further includes at least one end effector.

In certain embodiments the end effector is selected from the group consisting of barb, knot, pledget, and buttress. In other embodiments the end effector is a bulk of a material configured and dimensioned to limit movement of a distal segment of the loop in a proximal direction through tissue. In some embodiments, the end effector may be integral with the loop, alternatively, the end effector may be a separate device which is secured to the loop. In alternate embodiments, the end effector limits movement of at least a portion of the loop through tissue such that a segment of the loop remains outside a body tissue.

The anchoring device of the present disclosure may further include a needle secured to a proximal portion of the elongate body.

Another method for securing tissue is also provided, the method comprises the steps of providing an anchoring device, inserting a proximal portion of the medical device into tissue, pulling the two branches of the loop through tissue such that the two branches are simultaneously pulled through a penetration point; and, advancing the proximal portion of the loop through tissue such that the end effector limits movement of the distal portion of the loop through the tissue.

BRIEF DESCRIPTION OF DRAWINGS

Various preferred embodiments of the sutures are described herein with reference to the drawings, in which.

DETAILED DESCRIPTION OF EMBODIMENTS

Figure 1A:
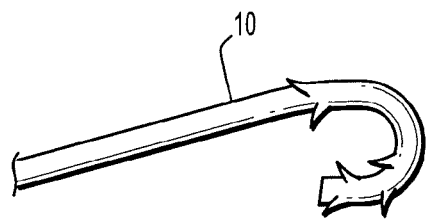
FIGS. 1A-1B are side views illustrating one embodiment of a looped suture.

The present disclosure is directed to an anchoring device and in certain preferred embodiments, a suture, herein referred to as an anchoring suture. The anchoring sutures of certain embodiments of the present disclosure have an elongate body, which connects to a needle at a proximal end thereof, and a distal end of the elongate body forms an anchoring loop. The anchoring loop further includes a plurality of anchors (tissue engaging members). Medical devices of the present disclosure include sutures formed from fibers, filaments, and yarns.

Anchoring devices, including anchoring sutures of the present disclosure may be absorbable or non-absorbable. It should be understood that combinations of filaments made from different materials (e.g. natural and synthetic, or bioabsorbable and non-bioabsorbable materials) may be used to make the present anchoring suture.

Suitable synthetic absorbable materials include polymers such as those made from lactide, glycolide, caprolactone, valerolactone, carbonates (e.g., trimethylene carbonate, tetramethylene carbonate), dioxanones (e.g., 1,4-dioxanone), 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, orthoesters, hydroxy alkanoates, tyrosine carbonates, polyimide carbonates, polyimino carbonates such as poly(bisphenol A-iminocarbonate) and poly(hydroquinone-iminocarbonate), and polymer drugs (e.g., polydiflunisol, polyaspirin, and protein therapeutics) and copolymers and combinations thereof. Suitable natural absorbable polymers include collagen, cellulose and gut. In embodiments, glycolide and lactide based polyesters, including copolymers of lactide and glycolide may be used.

Suitable non-absorbable materials which may be used to form the anchoring sutures disclosed herein include non-absorbable natural materials such as cotton, silk, and rubber. Suitable non-absorbable synthetic materials include monomers and polymers derived from materials such as nylons, polyolefins such as polypropylene and polyethylene, ultra high molecular weight polyethylene (UHMWPE), polyamides, polyesters such as poly ethylene terephthalate (PET), polyaryletherketone, polyvinylidene difluoride (PVDF), acrylic, polyamides, aramids, fluropolymers, polybutesters, silicones, and polymer blends, copolymers thereof and combinations with degradable polymers. Polypropylene can also be utilized to form the suture. The polypropylene can be isotactic polypropylene or a mixture of isotactic and syndiotactic or atactic polypropylene. Additionally, non-absorbable synthetic and natural polymers and monomers may be combined with each other and may also be combined with various absorbable polymers and monomers to create fibers and filaments for the present anchored device.

In certain embodiments, anchoring devices, including anchoring sutures, may, in whole or in part (e.g. anchors) may be constructed using shape memory polymers. Suitable polymers used to prepare hard and soft segments of shape memory polymers include polycaprolactone, dioxanone, lactide, glycolide, polyacrylates, polyamides, polysiloxanes, polyurethanes, polyether amides, polyurethane/ureas, polyether esters, and urethane/butadiene copolymers and combinations thereof.

In some embodiments, the sutures may include metals (e.g. steel and degradable magnesium), metal alloys or the like.

As used herein, the terms "fibers", "filaments" and "yarns" each may be used to construct in whole or in part anchoring devices. The term "fibers," in this context, are generally used to designate natural or synthetic structures that have a length approximately 3 orders of magnitude greater than their diameter or width. The term "filaments" are typically used to describe "fibers" of indefinite or extreme length, and "yarns" as a generic term for a continuous strand of twisted or untwisted "fibers" or "filaments" in a form suitable for knitting, weaving, braiding or otherwise intertwining.

Sutures of the present disclosure may be monofilament or multifilament (e.g. braided). Methods for making sutures from these suitable materials are within the purview of those skilled in the art (e.g. extrusion and molding). The filaments may be combined to create a multifilament suture using any technique within the purview of one skilled in the art such as commingling, twisting, braiding, weaving, entangling, and knitting. For example, filaments may be combined to form a yarn or they may be braided. In another example, filaments may be combined to form a yarn and then those multifilament yarns may be braided. Those skilled in the art reading this disclosure will envision other ways in which filaments may be combined. Fibers may also be combined to produce a non-woven multifilament large diameter suture. In certain embodiments, a multifilament structure useful in forming an anchoring suture according to the present disclosure may be produced by braiding. The braiding can be done by any method within the purview of those skilled in the art. For example, braid constructions for sutures and other medical devices are described in U.S. Pat. Nos. 5,019,093; 5,059,213; 5,133,738; 5,181,923; 5,226,912; 5,261,886; 5,306,289; 5,318,575; 5,370,031; 5,383,387; 5,662,682; 5,667,528; and 6,203,564; the entire disclosures of each of which are incorporated by reference herein. Furthermore, the anchoring device may include portions which are monofilament and portions which are multifilament. In some embodiments, the proximal end of the elongate body may be a multifilament and the looped portion (loop portion described below) may be a monofilament.

Additionally, the anchoring device may include biologically acceptable additives such as plasticizers, antioxidants, dyes, dilutants, bioactive agents and combinations thereof, which can be coated on the filaments or fibers, or impregnated into the fibers or filaments (e.g. during compounding or extrusion) used to form the anchoring suture of the present disclosure.

Various compositions and materials may also be applied to the anchoring sutures or included in the filaments or fibers to improve mechanical properties such as handling and knot strength or to deliver medicinal agents. Suitable coating materials include any materials conventionally applied to sutures. For example, suitable materials include fatty acid esters which may be combined with the metal salt of a fatty acid in the coating composition. Such esters include, for example, calcium stearate, stearoyl lactylate esters, palmityl lactylate esters, oleyl lactylate esters such as calcium, magnesium, aluminum, barium, or zinc stearoyl lactylate, calcium, magnesium, aluminum, barium, or zinc palmityl lactylate; calcium, magnesium, aluminum, barium, or zinc oleyl lactylate; with calcium stearate and calcium stearoyl-2-lactylate (such as the calcium stearoyl-2-lactylate commercially available under the trade name VERV from American Ingredients Co., Kansas City, Mo.) being preferred. When desirable, the fatty acid ester may be combined with a solvent. Suitable solvents include polar and non-polar solvents including but not limited to alcohols (e.g., methanol, ethanol, propanol), chlorinated hydrocarbons (such as methylene chloride, chloroform, 1,2-dichloro-ethane), and aliphatic hydrocarbons such as hexane, heptene, ethyl acetate.

In embodiments, the anchoring device may be combined with and/or coated with suitable materials including polyalkylene oxides such as polyethylene oxide, polypropylene oxide, polyethylene glycol (PEG), polypropylene glycol, copolymers thereof, and the like, including those having acrylate groups such as acrylate PEGs, and acrylate PEG/PPG copolymers. Such combinations may include blends or copolymers with polyalkylene oxide oligomers or polymers or other non-toxic surfactants. The resulting composition may possess antimicrobial properties due to the presence of the copolymers described above. In other embodiments, the sutures may be combined with silicone acrylates. Coatings may be applied to the individual filaments or the anchoring suture at any time prior to sterilization techniques. Coatings can be applied to the filaments using any technique within the purview of those skilled in the art.

Additionally, the anchoring device may incorporate various pharmaceuticals and medicinal agents. Medicinal agents and drugs may be applied to the sutures and/or construct materials by methods within the purview of those skilled in the art, including but not limited to dipping, spraying, brushing, vapor deposition, coextrusion, capillary wicking, film casting, molding and the like. Additionally, solvents may be used to incorporate various agents into the anchoring suture. Suitable solvent include those listed above.

Medicinal agents which may be incorporated into the device include antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes antibiotics, quorum sensing blockers, surfactants, metal ions, antimicrobial proteins and peptides, antimicrobial polysaccharides, antiseptics, disinfectants, anti-virals, anti-fungals, and combinations thereof.

Agents may be incorporated into a coating using solvents or mixed with various monomers or polymers and applied to the anchoring device. Additional suitable medicinal agents which may be used include colorants, dyes, preservatives, protein and peptide preparations, protein therapeutics, polysaccharides such as hyaluronic acid, lectins, lipids, probiotics, antibiotics, angiogenic agents, anti-thrombotics, anti-clotting agents, clotting agents, analgesics, anesthetics, wound repair agents, chemotherapeutics, biologics, anti-inflammatory agents, anti-proliferatives, diagnostic agents, antipyretic, antiphlogistic and analgesic agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and anti-anxiety agents, vitamin D preparations, hypoglycemic agents, antiulcer agents, hypnotics, antibiotics, antifungal agents, sedative agents, bronchodilator agents, antiviral agents, dysuric agents, brominated or halogenated furanones, and the like. In embodiments, polymer drugs, i.e., polymeric forms of such compounds for example, polymeric antibiotics, polymeric antiseptics, polymeric chemotherapeutics, polymeric anti-proliferatives, polymeric antiseptics, polymeric non-steroidal anti-inflammatory drugs (NSAIDS), and the like may be utilized and combinations thereof.

The anchoring device of the present disclosure can additionally contain suitable medicinal agents such as viruses and cells, peptides, polypeptides and proteins, analogs, muteins, and active fragments thereof, such as immunoglobulins, antibodies (monoclonal and polyclonal), cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.) hormones and hormone analogs (e.g., growth hormone), vaccines (e.g., tumoral, bacterial and viral antigens), somatostatin, antigens, blood coagulation factors, growth factors, protein inhibitors, protein antagonists, and protein agonists, nucleic acids, such as antisense molecules, DNA, RNA, oligonucleotides, polynucleotides and ribozymes and combinations thereof.

Methods for combining these medicinal agents with compositions of the present disclosure are within the purview of those skilled in the art and include, but are not limited to mixing, blending, dipping, spraying, wicking, solvent evaporating and the like.

In the description that follows, the term "proximal" as used herein, means the portion of the device which is nearer to the user, while the term "distal" refers to the portion of the device which is further away from the user.

Sutures of the present disclosure include an elongate body, having both distal and proximal portions, the distal portion of which transitions from the elongate body to an anchoring loop. Methods for creating anchoring loops are within the purview of those skilled in the art and include but are not limited to welding, ultrasonic energy, cutting, molding and gluing. In preferred embodiments to be described later, the anchoring loop includes barbs along a surface.

Adjuncts to making loops, such as adhesives and glues, may also be employed in the anchoring suture. In some embodiments (FIGS. 1A, 1B), the distal portion of suture may be folded and fixed to elongate body using adhesives and glues. In alternate embodiments, as shown in FIGS. 2A and 2B, loop portion may initially be a separate component which connects to an elongate body and optionally glued in place. It should be understood that embodiments and methods described in FIGS. 1 and 2 can be used to create any of the anchoring suture embodiments described herein (FIGS. 3-6). Suitable materials such as absorbable and non-absorbable materials include, but not limited to cyanoacrylates, isocyanates, polyurethanes, polyamines, polyamides, polyacrylates, polymethacrylates, silicones, carbonates, and other synthetic monomers and polymers and combinations thereof.

Adhesives such as cyanoacrylates can be employed in creating sutures of the present disclosure. Suitable cyanoacrylates include materials derived from methyl cyanoacrylate, ethyl cyanoacrylate, butyl cyanoacrylate, octyl cyanoacrylate, isobutyl cyanoacrylate, and methoxypropyl cyanoacrylate and combinations thereof and the like.

The anchoring loop further includes anchors disposed along a surface. Anchors can be created on the anchoring suture using any technique, including but not limited to lasers, molding, knives, blades, stamping, and other cutting means within the purview of those skilled in the art. Ultrasonic energy can also be used to create barbs or anchors as described in U.S. Patent Application No. 60/994,173 filed on Sep. 17, 2007 entitled "Method of Forming Barbs on a Suture" the entire disclosures of which are incorporated by reference herein.

Figure 1B:
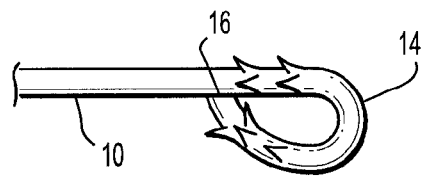
Figure 2A:
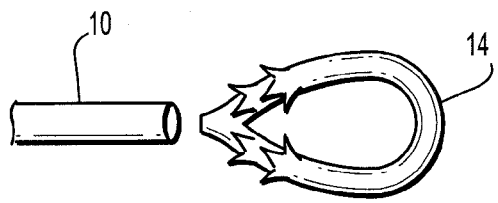
FIGS. 2A-2B are side views illustrating another embodiment of a looped suture.
Figure 2B:
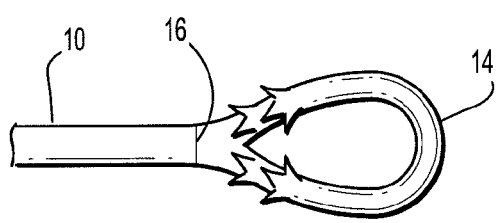
Figure 3:
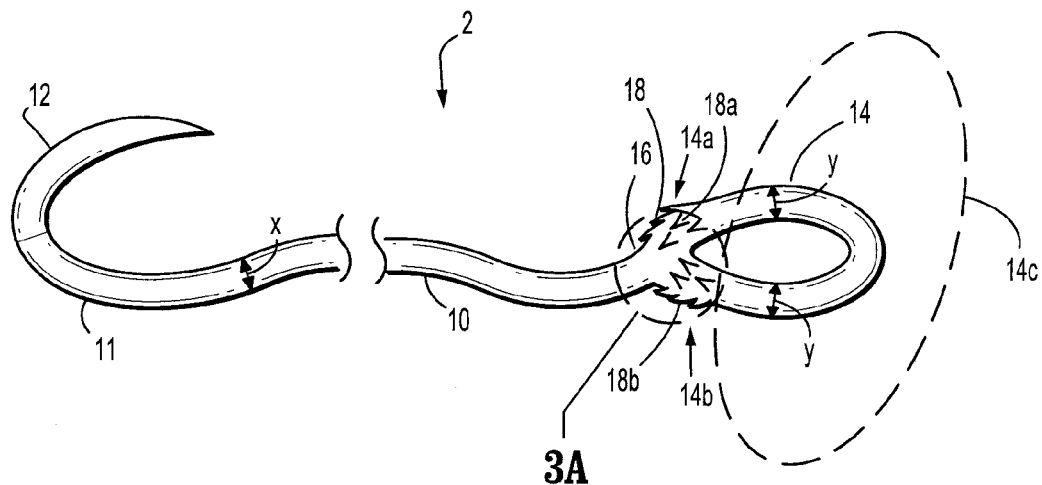
FIG. 3 is a side view illustrating one embodiment of an anchoring suture including barbs.

In some embodiments, anchoring sutures of the present disclosure include loops which are integral to an elongate body, as shown in FIGS. 1 and 3. Sutures with integral loops may be defined as having one structure or component in which the elongate body is continuous with the loop. For example, FIG. 1 shows an elongate body 10 in which the distal end is folded or "looped" to create a loop 14 (FIG. 1B) at the distal end of the medical device. The suture as shown in FIGS. 1 and 2 further includes transition area 16 and anchors which will be described in further detail below. An anchoring suture may also contain an integral loop as shown in FIG. 3, wherein the loop portion may be molded. In alternate embodiments, such as FIG. 2, anchoring sutures may comprise two components which are fixed or fitted together in a fashion as to create the anchoring suture. For example, the elongate body 10 may include a female component while the loop 14 may include a male component and the two components may be fitted together to create a final product. One skilled in the art can envision other manufacturing processes in which to create integral loops and medical devices with integral and non-integral loops.

Figure 3A:
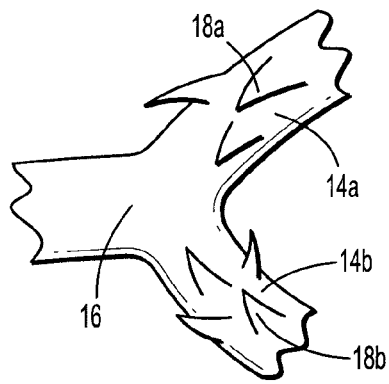
FIG. 3A is an enlarged view of the area of detail designated in FIG. 3.

Another embodiment of the anchoring suture of the present disclosure is shown in FIG. 3 and is designated generally by reference numeral 2. Suture 2 has an elongate body 10, a proximal portion of elongate body 10 terminating in a free end 11, and a distal portion of the elongate body 10 which forms, transitions into, or terminates in a loop 14. As shown in FIG. 3, the free end 11 further comprises a needle 12. The elongate body 10 has a diameter "x" and, in preferred embodiments, the elongate body 10 is generally elliptical in transverse cross-section. The distal end of elongate body 10 extends into a loop 14, bifurcating at transition area 16 (FIGS. 3 and 3*a*). Loop 14 includes two branches 14*a* and 14*b*, which may be identical in shape and cross-sectional area, to both each other and elongate body 10. In preferred embodiments, sections 14*a* and 14*b* are generally elliptical in shape and cross-sectional area, although other shapes are envisioned such as circular, oval, square, and rectangular. In the embodiment shown in FIG. 3, the loop 14 may be integral with the elongate body 10 of the suture 2. In alternate embodiments, the loop 14 may be a separate component prior to assembly (FIGS. 1 and 2), and during assembly the loop 14 may be attached to the elongate body 10. The loop 14 has a generally arcuate surface, and each branch (14*a* and 14*b*) has an independent diameter "y", of which 14*a* and 14*b* may be of similar or different diameters. The loop may be of any shape including circular, oval, polygonal.

Furthermore, anchoring suture of FIG. 3 includes a first plurality of anchors 18 disposed along a surface of the loop 14. Anchors 18*a* are disposed along surface of branch 14*a* and anchors 18*b* are disposed along branch 14*b*. Additionally, segment 14*c* is used to designate a loop segment in which barbs are absent. In the illustrated embodiment, anchors 18 are located adjacent transition area 16 of elongate body 10 and anchoring loop 14. Furthermore, the first plurality of anchors 18 is oriented such that movement of the anchoring loop 14 towards the proximal end is limited. As shown in FIG. 3, anchors 18 are oriented towards transition area 16 to prevent movement of anchoring loop 14 through tissue. In embodiments shown, anchors 18 are integral to the anchoring loop 14.

Figure 4:
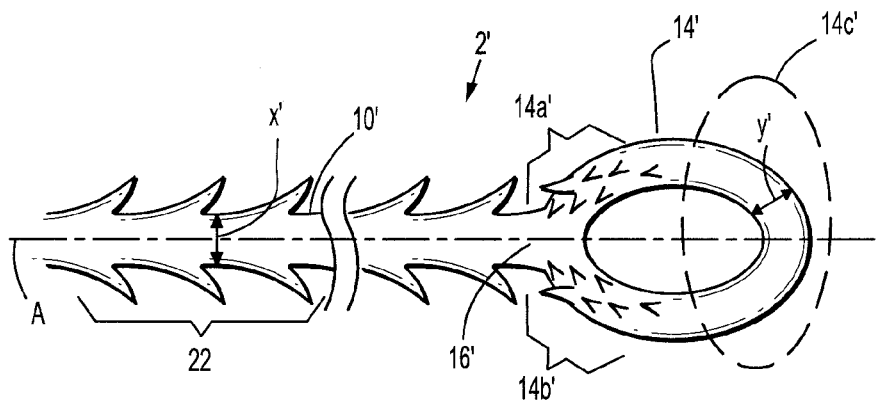
FIG. 4 is a side view illustrating an alternate embodiment of an anchoring suture including barbs.

It will be understood that FIG. 4 is a generally similar to FIG. 3 and therefore all numerals and descriptions which are the same in FIG. 3 are designated with the prime mark and have some differences. FIG. 4 shows an alternate embodiment of an anchoring suture 2' in which a second plurality of anchors 22 is disposed along the elongate body 10'. The second plurality of anchors 22 extends in the second direction which is different from a first direction of the first plurality of anchors. In the embodiment shown, the first plurality of anchors 18' are disposed along a loop surface and extend in the first direction, generally towards transition area 16' of the anchoring suture 2'. The second plurality of anchors 22 extend in a second direction, towards the loop 14', with respect to longitudinal axis A of the elongate body 10. As shown in FIG. 4. the first plurality of anchors 18' and the second plurality of anchors 22 extend in directions substantially opposite to one another. The second plurality of anchors 22 permits movement of the elongate body 10' in the direction of the leading or proximal end while preventing movement of the elongate body 10' towards the loop end.

Figure 5:
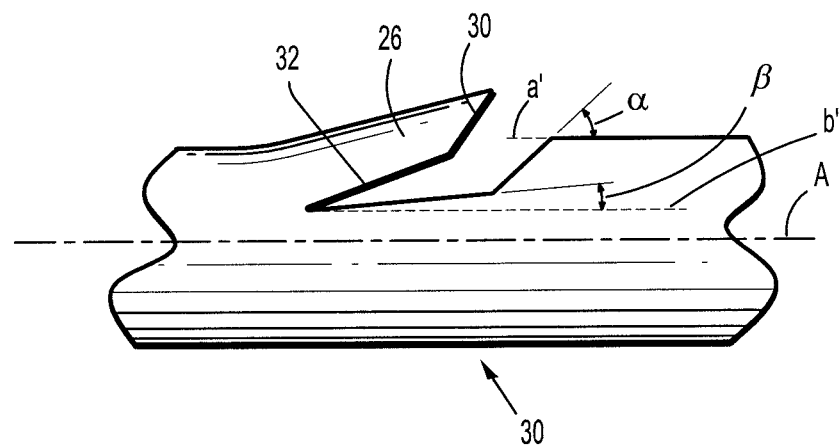
FIG. 5 is an enlarged side view showing a barb of an alternate embodiment of an anchoring suture with a compound barb; and, FIG. 6 is a side view illustrating another embodiment of an anchoring suture including barbs.

In the alternate embodiment shown in FIG. 5, anchoring suture 30 includes a compound barb 26 having an inner surface 30 including a first angle α, disposed at a first orientation relative to a longitudinal axis "A'" of the elongate body and a second angle β having a second inner surface 32, disposed at a second orientation relative to a longitudinal axis b of the elongate body. The anchoring suture may optionally include a third orientation (not shown). In the embodiment shown, the first, second and third orientations are each disposed at different angles with respect to the longitudinal axis. In some embodiments, the anchoring suture may include a staggered arrangement of large or small barbs. In other embodiments, an anchoring suture may have a random configuration of both large and small barbs. It will be understood that the embodiment shown in FIG. 5 is generally similar to FIGS. 3 and 4, but has a different geometry for the barbs. In alternate embodiments, the above-mentioned compound barb geometry may also be present on the anchoring loop (not shown).

The surface area of the plurality of anchors can also vary. For example, fuller-tipped anchors can be made of varying sizes designed for specific surgical applications. When joining fat and relatively soft tissues, larger anchors may be desired, whereas smaller anchors may be more suitable for collagen-dense tissues. In some embodiments (FIG. 4), a combination of large and small anchors within the same structure may be beneficial, for example when a fiber is used in tissue repair with differing layer structures. Use of the combination of large and small anchors with the same fiber wherein anchor sizes are customized for each tissue layer will ensure maximum holding properties.

Figure 6:
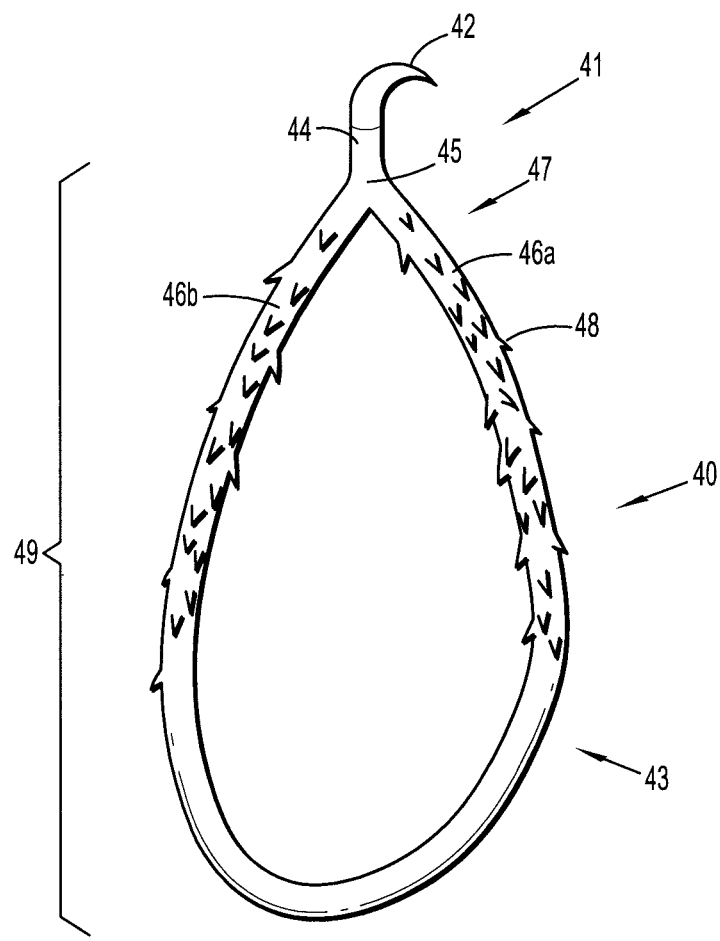

Another embodiment of an anchoring device is shown in FIG. 6. The anchoring device 40 includes a needle 42 at a proximal end 41 of the device. The device bifurcates at a transition area 45, and a distal portion of the device terminates in an anchoring loop 49. The anchoring loop 49 includes two branches 46*a* and 46*b* at a proximal end 47 of the anchoring loop 49. The anchoring loop 49 has a generally arcuate surface, branches 46*a* and 46*b* may have similar or different diameters. In the illustrated embodiment, a first plurality of anchors 48 are located adjacent the transition area 45. Furthermore, the first plurality of anchors 48 is oriented such that movement of the anchoring loop 49 in tissue, in a direction towards the distal end 43 of the device, is limited. As illustrated in FIG. 6, the device may have an elongate body 44 that is shorter in longitudinal length as compared to the anchoring loop 49. The two branches of the loop may be advanced through a single needle penetration point and pulled through tissue; the method of which will be described in detail later.

Figure 7:
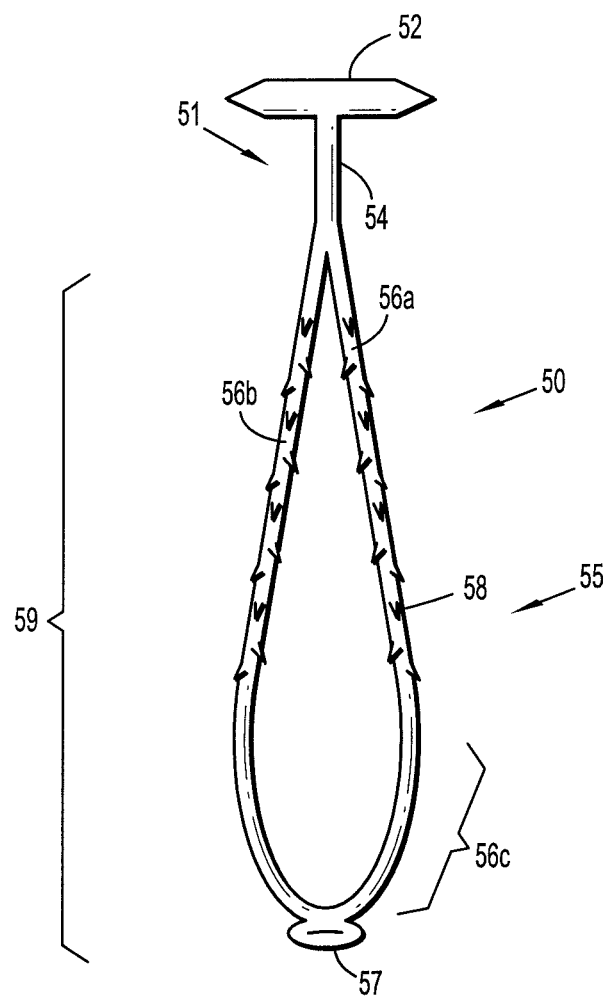
FIG. 7 is a side view illustrating an alternate embodiment of an anchoring suture with an end effector.

FIG. 7 illustrates an alternate embodiment of an anchoring device 50 which may be used in combination with a mechanical suturing device such as an Endo Stitch™ suturing device commercially available from Tyco Healthcare Group LP. Anchoring device 50 includes a needle 52 which is compatible with a mechanical suturing device such as an Endo Stitch™ suturing device. The proximal portion 51 of the anchoring suture includes an elongate body 54, and the distal portion 55 of the suture terminates in a loop 59. The loop 59 includes two branches 56a and 56b and each branch includes a plurality of barbs 58 on a surface thereof. In other embodiments, a plurality of barbs may only be on a surface of at least one branch or a portion of the anchoring device. The loop 59 also includes an unbarbed distal portion 56c. The loop further includes an end effector 57 which limits movement of the anchoring device through tissue. In some embodiments, the end effector is located on the unbarbed distal portion 56c of the loop (FIG. 7). As illustrated, the end effector 57 is a bulk (large mass) of suture material, which is generally "T"-shaped and in the current embodiment, the end effector is welded to the loop 59.

Figure 8C:
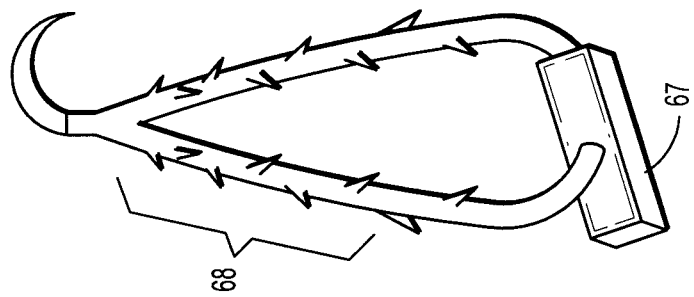
FIG. 8C is a side view of an alternate embodiment of an anchoring suture with an end effector.
Figure 8B:
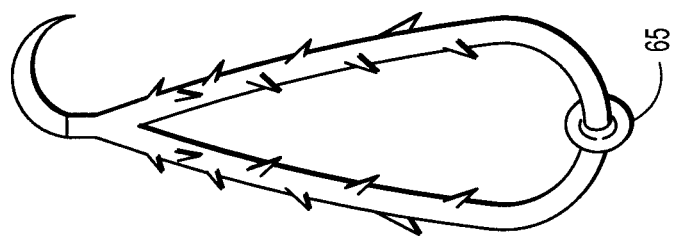
FIG. 8B is a side view of a different embodiment of an anchoring suture with an end effector.
Figure 8A:
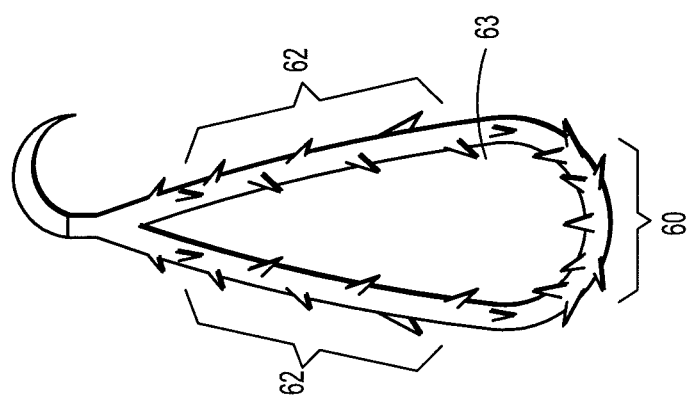
FIG. 8A is a side view of another embodiment of an anchoring suture with an end effector.

This disclosure contemplates different end effectors and non-limiting alternate embodiments are illustrated in FIGS. 8A, 8B and 8C. In FIG. 8A an end effector is illustrated as a second plurality of barbs 60 which are oriented such that movement of an end portion of the loop 63 through tissue towards a proximal end of the anchoring suture is limited. In this embodiment, a first plurality of barbs 62 located at a proximal portion of the loop 63 are shown oriented in a generally opposite direction to a second plurality of barbs 60, which are located at a distal portion of loop 63. In another embodiment, FIG. 8B, the end effector is a bead 65 of a polymeric material. In some embodiments, the bead may of a similar material to the anchoring loop and in alternate embodiments; the bead may be comprised of a different material than the anchoring loop. In some embodiments, such as FIGS. 8A and 8B, the end effector is integral with the loop. In yet other embodiments, the end effector may be a separate device such as a pledget or buttress. As illustrated in FIG. 8C, the end effector is a pledget 67 formed on or otherwise attached to the loop. In this embodiment, prior to creating a loop, a suture may penetrate the pledget 67 and a length of the suture may be pulled through the pledget. It should be noted that once the pledget has been moved across a portion of barbs 68 projecting from the suture surface, the barbs will prevent the pledget from disengaging the suture and the barbs will retain the pledget in place on the suture. Next, a loop may be created via various means including those described above, and the pledget 67 may be positioned at a distal most point of the anchoring loop. It should be understood that end effectors are not limited to those structures described herein and one skilled in the art may contemplate other shapes and devices which may be used for a similar purpose. End effectors may be constructed using methods within the purview of those skilled in the art, including but not limited to glues, adhesives, lasers, ultrasonic or heat welding, molding, overmolding and the like. Any of the suture materials and structures discussed above may be used to form the anchoring devices discussed herein.

As used herein, the term "tissue" includes, but is not limited to, tissues such as skin, fat, fascia, bones, muscles, tendons, ligaments, organs, nerves, and blood vessels. Also used herein, the term "wound" includes, but is not limited to, a surgical incision, cut, laceration or severed tissue in human or animal skin or other human or animal bodily tissue.

Figure 9A:
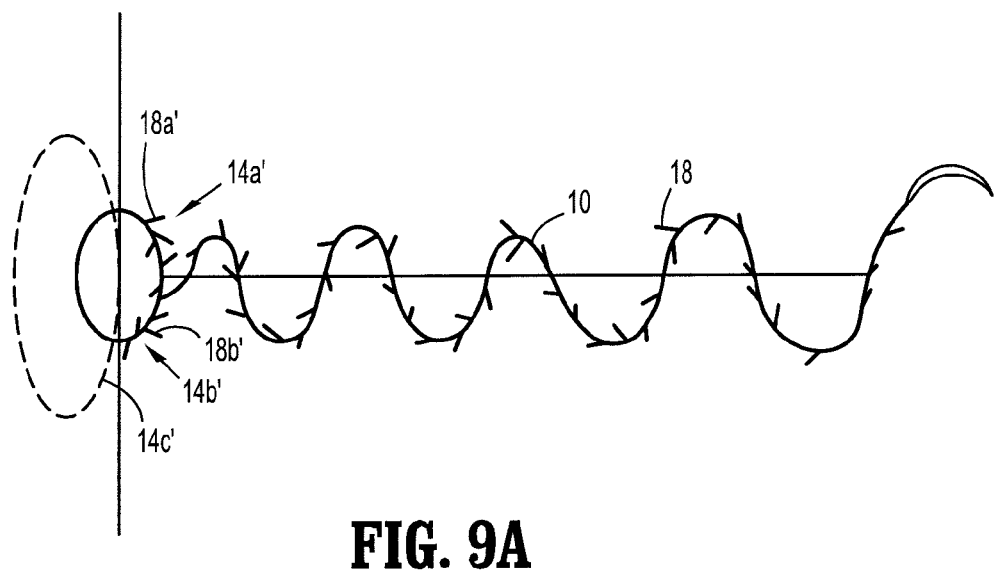
FIG. 9A is a plan view of the anchoring suture of FIG. 4 in tissue with portions of tissue removed.
Figure 9B:
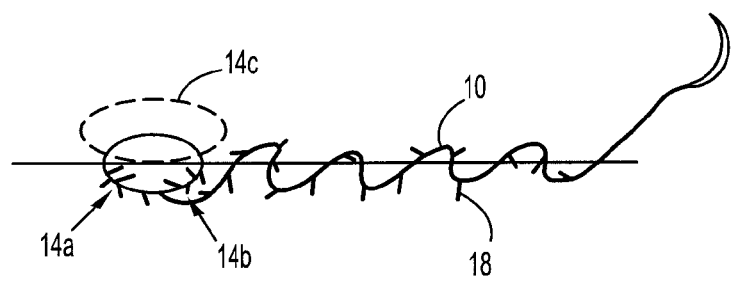
FIG. 9B is a side view of the anchoring suture of FIG. 4 in tissue with portions of tissue removed.

Tissue may be sutured by inserting proximal portion of an anchoring suture into tissue at a first section and advancing the proximal portion of the suture through a second section of the tissue, and exiting tissue at an exit point. The suture is pulled through the exit point until the first plurality of barbs on the anchoring loop engages tissue and resists movement in direction of needle advancement, thus preventing further advancement of anchoring loop through tissue. The proximal portion of the suture may optionally be inserted through the segment of the loop remaining outside the body tissue for enhanced fixation. FIGS. 9A and 9B show the embodiment of FIG. 4, where an unbarbed loop segment 14c' remains exterior to the wound site (or external to skin in dermal closure) due to the anchors 18a' and 18b' and lack of anchors on segment 14c'. It should be understood that all embodiments described herein can be used in a similar fashion. Upon exit of tissue, needle and proximal end of suture may be passed through segment of loop which remains exterior to wound site to secure suture in place. User may then continue suturing wound, entering and exiting tissue until wound site is closed (or implant attached).

Figure 10A:
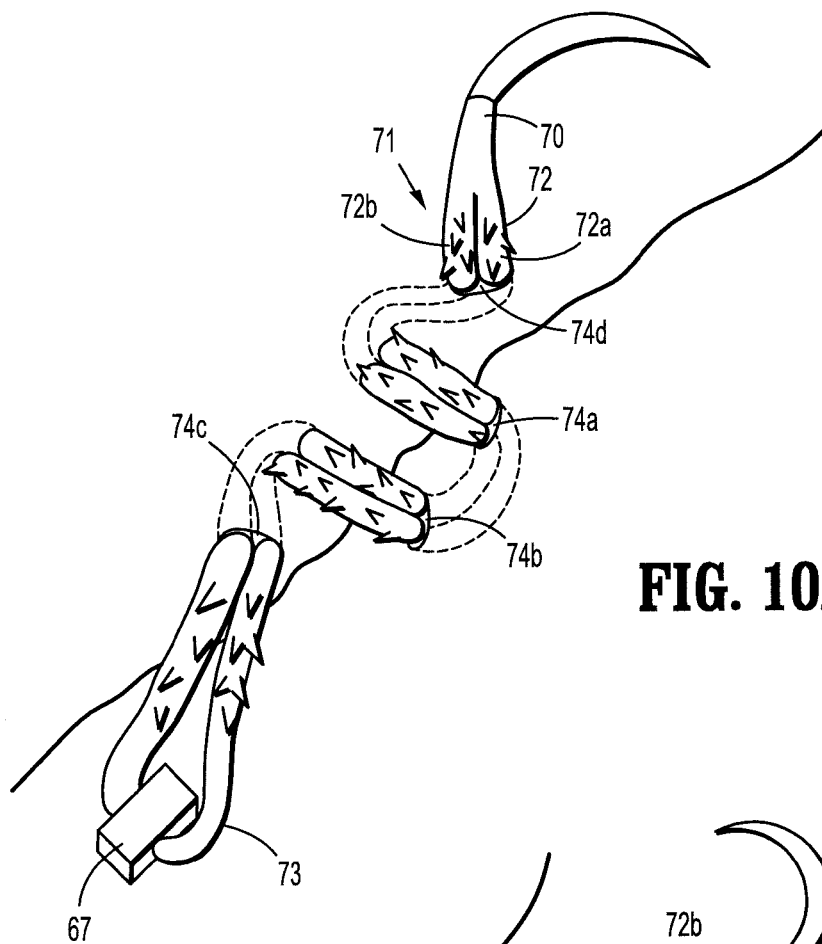
FIG. 10A is a plan view of the anchoring suture of FIG. 8C in a first position in tissue, with portions of tissue removed.
Figure 10B:
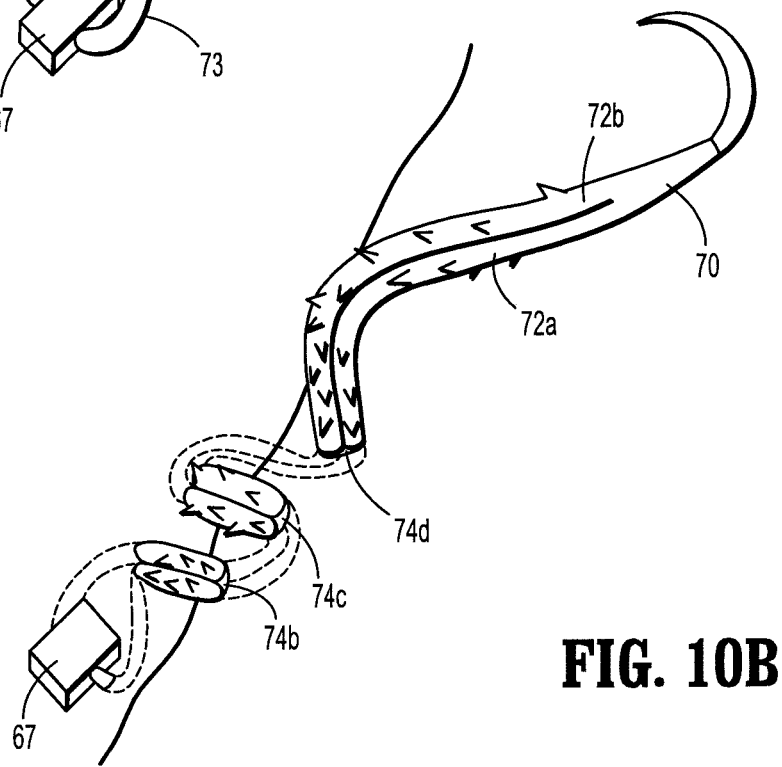
FIG. 10B is a plan view of the anchoring suture of FIG. 8C in a second position in tissue, with portions of tissue removed.

FIGS. 10A and 10B illustrate the embodiment of FIG. 8C in tissue. Tissue may be secured in a similar manner as described above, by inserting a proximal portion of the anchoring device into tissue at a first section and advancing the proximal portion of the anchoring device, including a proximal portion of the loop, through a second section of the tissue, and exiting tissue at an exit point. In the embodiments described in FIGS. 6, 7, 8A, 8B, and 8C once the needle is advanced through tissue, the remainder of the suture follows including the two branches of the loop. More specifically, the two branches of the loop are advanced through a needle penetration point (or points through which the needle and elongate body have passed). FIG. 10A illustrates a first position of the embodiment of an anchoring device as described in FIG. 8C. As illustrated, proximal portion of suture 70 and proximal portion 71 of loop 72, including two branches 72a and 72b, are advanced through tissue. Both branches 72a and 72b are advanced through needle penetration points (74a, 74b, 74c, and 74d), the barbs engage tissue and suture holding force is increased. FIG. 10B shows the embodiment of FIG. 8C in a second position. Once the anchoring suture has been further advanced through tissue, the pledget 67 prevents any further movement of the distal loop portion through tissue. It should be understood that other embodiments of end effectors and shown and described would function in a manner similar to the embodiment described with respect to FIGS. 10A and 10B. It should also be understood that anchoring sutures without end effectors may also be inserted and advanced through tissue in a similar manner.

Figure 11B:
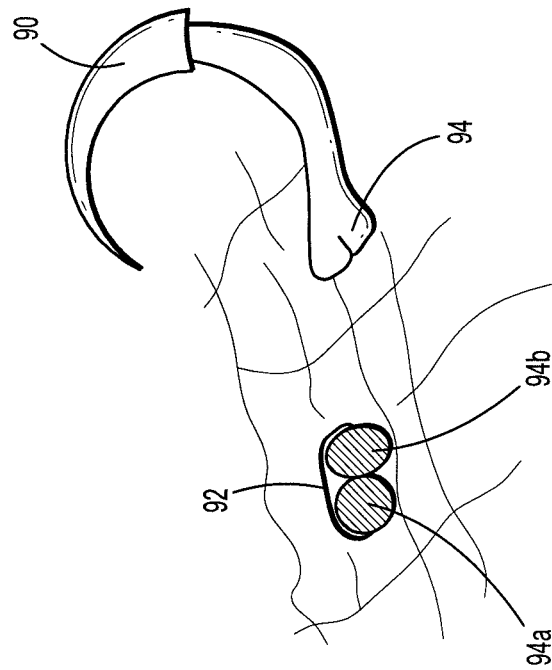
FIG. 11A shows a perspective view, partially in cross-section, of a suture filling a needle penetration point; and, FIG. 11B shows a perspective view, partially in cross-section, of an anchoring suture of the present disclosure filling a needle penetration point.
Figure 11A:
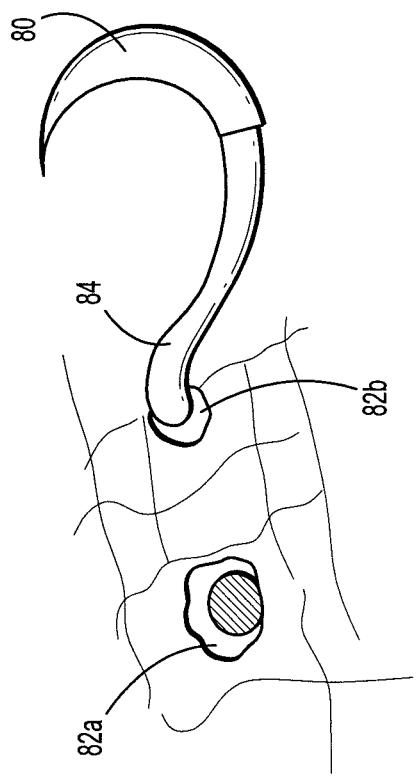

FIG. 11A shows the prior art in which an oversized needle 80 penetrates tissue, and leaves a tissue penetration point (82a and 82b) that a single suture strand 84 may not fill. FIG. 11B shows one embodiment of the current disclosure in which an oversized needle 90 penetrates tissue and the two branches (94a and 94b) of the anchoring device 94 can better fill the needle penetration point 92. The two branches of the loop in combination with the barbs allow an increase in tissue holding strength which may be desirable in certain applications.

In order to facilitate needle attachment to an anchoring suture or device of the present disclosure, conventional tipping agents can be applied to the braid. Two tipped ends of the fiber may be desirable for attaching a needle to each end of the fiber to provide a so-called double armed suture. The needle attachment can be made by any conventional method such as crimping, swaging, etc, as is known within the purview of those skilled in the art. Alternatively, a reduced diameter may be provided at the end of the suture to be inserted into the drilled end of a needle. To provide a reduced diameter, the suture may by machined using any technique within the purview of those skilled in the art, such as cutting, grinding, laser machining or the like.

Anchoring devices, including anchoring sutures of the present disclosure may be employed in medical devices, drug delivery devices and cell growth substrates. Examples of suitable medical devices and/or surgical devices employing the anchoring sutures may include, but are not limited to meshes, wound dressings, bandages, drug delivery devices, anastomosis rings, stents, grafts, catheter systems, soft tissue repair and augmentation devices, scaffolds, buttresses, lap bands, tapes, anchors, ribbons, orthopedic devices, tissue engineering scaffolds, various cell growth substrates, and other implantable devices. In some embodiments, devices of the present disclosure may be knitted or woven with other fibers, either absorbable or non-absorbable, to form surgical devices. The anchoring devices and/or sutures also can be made into meshes or non-woven materials to form fabrics, such as matted fabrics and felts.

Additionally, anchoring devices of the present disclosure may be packaged using materials known to those within the purview of those skilled in the art, including foil and various plastics (e.g. polyethylene), which may provide a moisture barrier.

Once the anchoring device is constructed, it can be sterilized by any means within the purview of those skilled in the art including but not limited to ethylene oxide, electron beam (e-beam), gamma irradiation, autoclaving, and the like.

Example 1

Distal end of Maxon™ suture is folded towards elongate body to create a loop, and suture (loop) is then placed in an ultrasonic welding apparatus, where loop is welded closed. Suture is then affixed to an ultrasonic cutting apparatus to create barbs. Elongate body and anchoring loop of anchoring suture is cut via ultrasonic blades at various angles.

Example 2

Distal end of Surgipro™ suture is folded towards elongate body to create loop and glue is placed on elongate body and distal suture end is folded over and attached to elongate body, creating a fixed loop. Suture is then affixed to a cutting apparatus and anchoring suture is cut at various angles using a knife. Anchoring suture is then coated with a chemotherapeutic agent using solvent casting.

Example 3

Distal end of Maxon™ suture is folded towards elongate body to create a loop, and suture (loop) is then placed in an ultrasonic welding apparatus, where loop is welded closed. The ultrasonic welding apparatus is then used to weld a distal end of the loop into a generally "T"-shape, creating an end effector. Suture is next affixed to an ultrasonic cutting apparatus to create barbs. Elongate body and a proximal portion of the anchoring loop of anchoring suture is cut via ultrasonic blades at various angles.

It should be noted that the present disclosure is not limited to wound closure and contemplates other procedures such as cosmetic and orthopedic procedures. Additionally, the above description contains many specifics; these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What we claim is:

1. A method for securing tissue, the method comprising:
   providing a suture having a proximal portion and a distal portion, wherein the proximal portion includes a single elongate body and the distal portion of the suture includes a loop, wherein at least a portion of the loop includes a first plurality of barbs extending in a distal direction and a second plurality of barbs extending in a proximal direction, the suture further includes a transition area defined by a bifurcation of the single elongate body into two branches of the loop;
   inserting the proximal portion of the suture into tissue at a penetration point;
   advancing the two branches of the suture through the tissue such that the two branches are simultaneously pulled through the penetration point;
   pulling the suture through tissue until movement of the loop through the tissue is limited by the second plurality of barbs; and,
   securing the suture in the tissue.

2. The method according to claim 1, wherein advancing the two branches of the suture through the penetration point increases the holding force of the suture in the tissue.

3. The method according to claim 1, wherein the two branches exert pressure on the tissue at the penetration point.

4. The method according to claim 1, wherein the second plurality of barbs limits movement of at least a portion of the loop through the tissue such that a segment of the loop remains outside the tissue.

5. The method according to claim 1, wherein the second plurality of barbs engages the tissue to prevent movement of the loop in a proximal direction.

6. The method according to claim 1, wherein the first plurality of barbs are disposed on a surface of the two branches of the suture.

7. The method according to claim 6, wherein the first plurality of barbs secure the two branches in the tissue.

8. The method according to claim 1, wherein inserting the proximal portion of the suture into the tissue at the penetration point includes directing a needle disposed on a free end of the single elongate body into the tissue at the penetration point.

9. A method for securing tissue, the method comprising:
   providing a suture having a single elongate body and a loop disposed on a distal end of the elongate body, the loop including a proximal portion and a distal portion, wherein the proximal portion includes a first plurality of barbs extending towards the distal portion and the distal portion includes a second plurality of barbs extending towards the proximal portion;
   inserting the single elongate body of the suture into tissue at a penetration point;
   advancing the proximal portion of the loop through the penetration point; and,
   pulling the suture through tissue until movement of the loop through the tissue is limited by the second plurality of barbs.

10. The method according to claim 9, wherein inserting the single elongate body of the suture into the tissue at the penetration point includes directing a needle disposed on a proximal end of the single elongate body of the suture into the tissue at the penetration point.

* * * * *